US005895647A

United States Patent [19]
Rollwagen

[11] Patent Number: 5,895,647
[45] Date of Patent: Apr. 20, 1999

[54] USE OF ORAL INTERLEUKIN-6 AS THERAPY FOR HEMORRHAGIC SHOCK

[75] Inventor: Florence M. Rollwagen, Woodfield, Md.

[73] Assignee: The United States of America as represented by the Secretary of the Navy, Washington, D.C.

[21] Appl. No.: 08/772,225

[22] Filed: Dec. 20, 1996

[51] Int. Cl.$^6$ ..................................................... A61K 38/20
[52] U.S. Cl. .......................... 424/85.2; 424/85.1; 514/2; 514/8; 514/921
[58] Field of Search ................................ 424/85.1, 85.2; 514/921

[56] References Cited

U.S. PATENT DOCUMENTS

| | | |
|---|---|---|
| 5,154,921 | 10/1992 | Sager et al. . |
| 5,188,828 | 2/1993 | Goldberg et al. . |
| 5,296,353 | 3/1994 | Ochoa et al. . |
| 5,426,181 | 6/1995 | Lee et al. . |
| 5,723,120 | 3/1998 | Brakenhoff ............................. 424/85.2 |

OTHER PUBLICATIONS

Baqar, S.et al. Dec. 1993. Modulation of Mucosal Immunity against *Campylobacter jejuni* by Orally administered Cytokines. Antimicrobial Agents and Chemotherapy, vol.37, No. 12, p.2688.

Rollwagen, F.M. et al., Use of Oral Cytokines to Alleviate Bacterial Translocation from the Gut Following Hemorrhage. The 9th International Congress of Immunology, Jul. 23–29, 1995, San Francisco, California, U.S.A., Abstract Book p. 136, Abstract No. 801.

VanSnick, J. Interleukin-6: an overview. Ann. Rev. Immunol. 8:253. 1990.

Ryffel, B., M.J. Mihatsch and G. Woerly. Pathology induced by IL–6. Int. Rev. Exp. Pathol. 34:79–89, 1993.

Heinrich, P.C., J.V. Castell and T. Andus. Interleukin–6 and the acute phase response. Biochem. J. 265:621–636, 1990.

Rollwagen FM, Li YY, Pacheco ND, Nielsen TB: Systemic bacteraemia following haemorrhagic shock in mice: alleviation with oral Interleukin–6, Cytokine vol. 8 No.2:121–129; 1996.

Rollwagen, F.M. et al., Orally Administered IL–6 as Prophylaxis for Sepsis Following Hemorrhagic Shock, Choque 96, Nov. 14, 1996, Sao Paulo, Brazil, Abstract No. S–6.

Cytokines in Health and Disease, ed Remick ed, 2nd ed, 1997, pp. 581–589.

Immunology, ed Kuby, 1992, p. 266.

Natanson et al., Annals of Internal Medicine, v. 120(9) 1994, p. 771.

*Primary Examiner*—Garnette D. Draper
*Attorney, Agent, or Firm*—A. D. Spevack; Daniel Kalish

[57] ABSTRACT

A method for ameliorating the effects of hemorrhagic shock in a subject consists of locally administering to the gut of the subject, at a selected time during the period of from about 5 hours before blood loss to about 5 hours after blood loss, a therapeutic amount of a cytokine.

21 Claims, 5 Drawing Sheets

USE OF ORAL INTERLEUKIN-6 AS THERAPY FOR HEMORRHAGIC SHOCK

FIELD OF THE INVENTION

This invention relates generally to bio-affecting and body treating drug compositions, and more particularly to amelioration of the adverse effects of hemorrhagic shock by administration of lymphokines.

BACKGROUND OF THE INVENTION

Severe trauma frequently results in massive blood loss leading to hemorrhagic shock. Survival following hemorrhagic shock has improved significantly with therapeutic interventions such as blood transfusion, rapid volume resuscitation, alteration of gut flora, and improved nutrition. However, infection remains a major cause of morbidity and mortality after severe hemorrhagic episodes.[1] Following hemorrhagic shock, the translocation of enteric bacteria to extraintestinal sites frequently contributes to sepsis and increases the risk of severe illness.[2]

Prolonged susceptibility to infection is often seen in subjects who have initially recovered from hemorrhagic shock. Hemorrhagic shock also may cause suppression or reduction of various immune functions, thus rendering the subject less able to cope with an increased bacterial influx and further endangering the subject.[3]

Therapy, such as intravenous antibiotic therapy and massive fluid infusion, which is directed towards alleviating post-shock infection, is of limited effectiveness because the initial damage, translocation of enteric bacteria and suppression of the immune response, have already been sustained. In one study, 89% of subjects developing sepsis after hemorrhage died of systemic septic shock despite such treatments.[4] It would be desirable to utilize therapy that minimizes the translocation of bacteria to extraintestinal sites, thus reducing post-shock infection.

SUMMARY OF THE INVENTION

It is an object of this invention to provide therapy for hemorrhagic shock which reduces the extraintestinal translocation of bacteria.

It is another object of this invention to provide therapy for hemorrhagic shock which reduces the extraintestinal translocation of bacteria and which enhances the subject's immune response.

These and additional objects of the invention are accomplished by ameliorating the effects of hemorrhagic shock in a subject by locally administering to the gut of the subject, at a selected time during the period of from about 5 hours before blood loss to about 5 hours after blood-loss, a therapeutic amount of a cytokine. This therapeutic treatment restores intestinal integrity and intestinal barrier capacity thus reducing the extraintestinal translocation of bacteria.

These and other objects, features and advantages of the present invention are described in or apparent from the following detailed description of preferred embodiments.

BRIEF DESCRIPTION OF THE DRAWINGS

The invention will be described with reference to the drawings, in which like elements have been denoted throughout by like reference numerals. The representations in each of the figures is diagrammatic and no attempt is made to indicate actual scales or precise ratios. Proportional relationships are shown as approximations.

DETAILED DESCRIPTION OF THE INVENTION

This invention constitutes oral administration of a therapeutic dose of a lymphokine so as to ameliorate the adverse effects of hemorrhagic shock. As used herein, the terms "lymphokine", "cytokine" and "chemokine" are considered synonymous.

In the preferred embodiment, the lymphokine used is interleukin-6 ("IL-6") and most practically, yeast derived, recombinant IL-6 (rIL-6). RIL-6 corresponding to IL-6 naturally occurring in humans, mice and other species is reported to exhibit multiple activities including enhancement of the immune response and acute phase reaction[5]. IL-6 is commercially available off-the-shelf in various forms, including recombinant human, rat and mouse IL-6 derived from transfected yeast, eukaryotic cells or viruses, and from various suppliers, including Genzyme, Endogen, R&D Systems or Intergen. The potency of IL-6 is measured in terms of immunologic activity, specifically the ability to promote the growth of IL-6 dependent cell lines[6]. This assay uses increasing amounts of IL-6 in culture until a maximum proliferative plateau is reached. The potency of various lots is then expressed as half-maximal units. In vivo or in vitro applications of IL-6 must be determined by the user in his/her own laboratory.

IL-6 of one species, such as human, is effective when administered to another species, such as mouse, rat or marmoset.[7]

As shown in the examples described below, an orally administered dose of mouse IL-6 has been shown to be effective in ameliorating the adverse effects of hemorrhagic shock in the murine model. Because of the above-described cross-species effectiveness, orally administered IL-6 also is effective in ameliorating the adverse effects of hemorrhagic shock in humans, other mammals and other animals. Administration of rIL-6 of the same species as the subject is preferable. Yeast derived rIL-6 of the same species as the subject is optimally effective because yeast-derived rIL-6 is glycosylated (sugar molecules are attached), thus rendering it resistant to proteolytic enzymes in the digestive system. IL-6 such as that derived from viruses or bacteria is typically not glycosylated, since these organisms lack the specific enzymes necessary for the attachment of sugar molecules to the protein backbone.

To ameliorate the effects of hemorrhagic shock the rIL-6 is orally administered in a therapeutically effective dosage.

As shown below in the Examples, such oral administration has been found effective in dosages as low as 2–3 nanograms (ng)/mouse, corresponding to a dosage 80–150 ng/kilogram (kg) of the animal's body weight for 20–25 gram (g) mice; and as high as 30 ng/mouse, corresponding to 1–1.5 micrograms (ug)/kg. Dosages as low as half the lower tested limit, that is, 40 ng/kg, and as high as twice the upper tested limit, that is 3 µg/kg, are also effective. The upper limit on the effective dosage is the dosage at which administration of rIL-6 has adverse effects on the subject. The upper limit on IL-6 administration by other than oral routes is in the range of 1 milligram (mg)/kg, an amount approximately 10,000 fold higher than the dose described in this invention. Such doses have not been found to be particularly harmful.[8] The therapeutically effective dosage of orally administered rIL-6 for the amelioration of hemorrhagic shock sepsis could be as high as 1 mg/kg. Thus, the minimum therapeutic dosage of yeast-produced recombinant interleukin-6 is about 40 ng/kg, preferably about 80 ng/kg, and most preferably about 150 ng/kg. The maximum therapeutic dosage of yeast-produced recombinant interleukin-6 is about 1 mg/kg, preferably about 3 µg/kg, more preferably about 1.5 µg/kg, and most preferably about 1 µg/kg.

IL-6 has a local effect on the gut thus alleviating the effects of hemorrhagic shock. Therefore the cytokine is administered locally to the gut, preferably by oral administration. Systemic administration of cytokine is expensive, and activates tissues and organs far from the organ of interest (the intestine).[9] In contrast, IL-6 is somewhat resistant to proteolytic enzymes in the small intestine, and oral administration targets the cytokine to enteric bacteria and repair of intestinal tissues.

IL-6 was administered orally to experimental animals as soon as the animals regained consciousness after the procedure. This time of administration was on the order of 1½ to 2 hours after the animals first lost blood. The cytokine IL-6 could be effectively administered even later than after 5 hours of shock following hemorrhage. A single administration of 100 ng/kg of IL-6 was effective. IL-6 is effective because it has vasodilation properties in addition to immunologic properties.

In theory, the adverse effects of hemorrhagic shock could be ameliorated by involuntary oral administration of IL-6 up to about 5 hours after the initial hemorrhage, or even later. Involuntary oral administration could very well save the life of an unconscious subject through the use of a naso-gastric tube.

Oral administration of is of most significant effectiveness in reducing the adverse effects of hemorrhagic shock for a period of about 5–6 hours after administration. Therefore, in theory, oral administration of IL-6 is a useful prophylactic up to about 5–6 hours before anticipated blood loss.

IL-6 belongs to a specific class of cytokines known as inflammatory mediators[10]. In theory, IL-6 is effective because it has vasodilation properties in addition to immunologic properties and so, other substances in this class might also be effective. Tests of various cytokines for their ability to reduce bacterial translocation following hemorrhage were performed using doses in the range of known biological activity for each cytokine. The cytokines TNF-a (Tumor necrosis factor-alpha), IL-1-b, IL-2 and IFN-g (Interferon-gamma) were tested and found to be ineffective in preventing bacterial translocation following hemorrhage. In particular, while anesthetized, the mice were hemorrhaged to 35 mm Hg blood pressure and held at that blood pressure for one hour. They were then resuscitated with shed blood and two-fold volume Lactated Ringer's Solution. Upon regaining consciousness, they were fed 0.5 ml fluid containing either IL-2 or TNF. The dosages ranged from $1 \times 10^4$ to $1.65 \times 10^4$ units/kg body weight for TNF, and $4 \times 10^3$ to $6.6 \times 10^3$ units/kg body weight for IL-2. This regime was found to be ineffective in preventing bacterial translocation following hemorrhage.

Oral administration of crude cytokine in the form of CAS, also called T-cell growth factor, is also effective in reducing the adverse effects following hemorrhagic shock, and CAS has this therapeutic effect by reducing extraintestinal bacterial translocation. Such a therapeutic regime is effective because CAS includes many cytokines, such as IL-2, IL-6, TNF, IFN-g and IL-5 as well as undiscovered mediators. Of these constituents, IL-6 has been shown to have the same effects, and IL-2, TNF and IFN-g have been shown ineffective in preventing bacterial translocation following hemorrhage.

Figure 1:
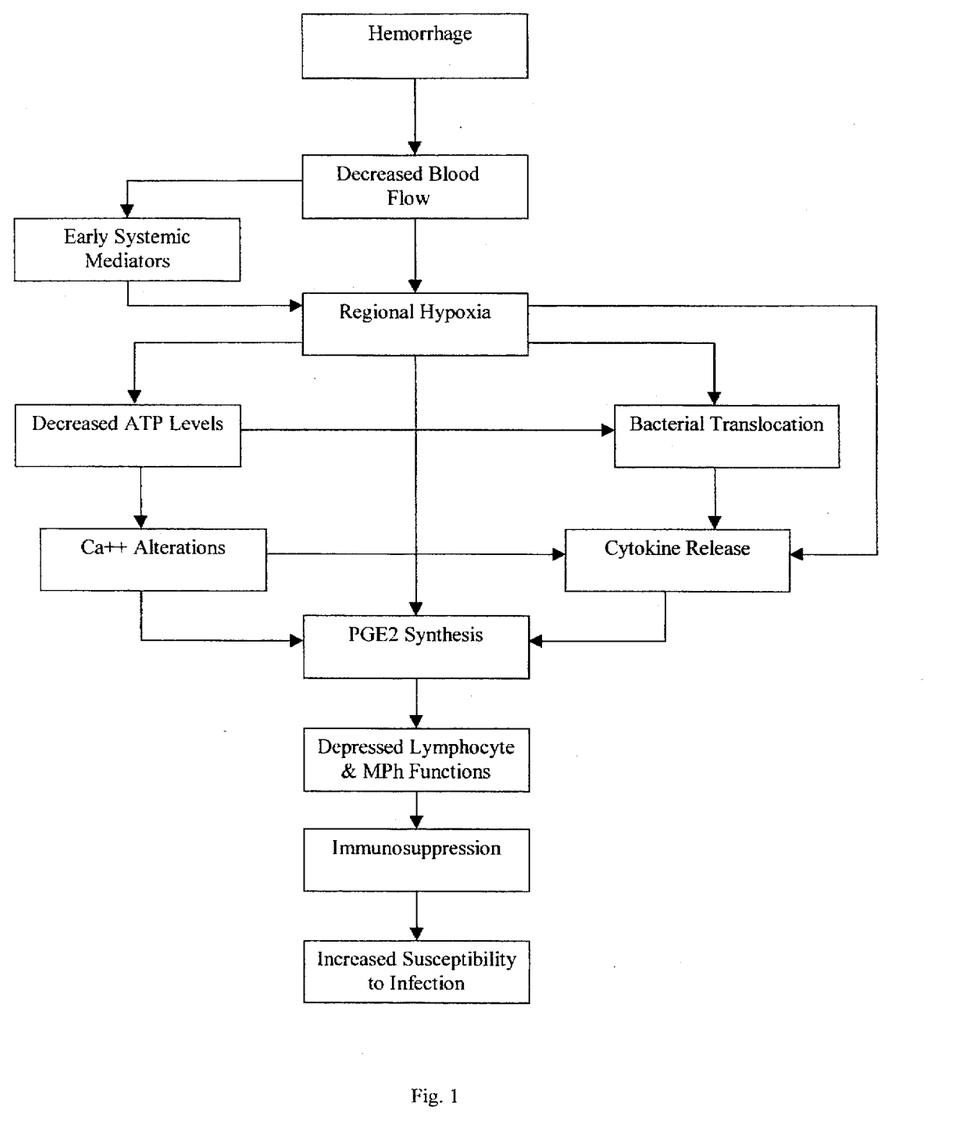
FIG. 1 is a schematic outlining the progressive changes occurring following rapid loss of blood (hemorrhage).

Referring now to FIG. 1, hemorrhage leads to decreased blood flow in all tissues. Although some attempt to preserve blood pressure is made by the hemorrhaged organism, if the insult is sufficiently severe, these compensatory mechanisms will be ineffective. In an effort to preserve brain function, circulation is shunted away from the intestine, leading to reduced oxygen flow to this tissue. Even though peripheral blood pressure may be restored by treatment in the Emergency Department, the intestinal blood flow remains shut down, leading to local hypoxia (reduction of oxygen content), also called regional hypoxia on FIG. 1.

One of the more sensitive tissues effected by blood loss is the intestine. Continuous proliferation and high oxygen consumption make a steady flow of oxygen essential. As soon as this flow is stopped, the cells become anoxic and begin to express early mediators (referred to as Early Systemic Mediators on the chart), such as the transcription factors c-jun, c-myc and c-fos. The reduction in oxygen leads to decreased ATP levels in the cell, thereby shutting down metabolic processes in a systematic way.[11] The production of these mediators leads to the breakdown of cellular structure including altered $Ca^{++}$ metabolism and loss of membrane integrity. Breakdown of cellular structure at the intestinal epithelial layer leads to translocation of bacteria and their products (endotoxin, lipopolysaccharide (LPS)), which leads to prostaglandin E-2 (PGE2) which leads to PGE2 synthesis and the beginning of systemic breakdown leading to multiple organ failure (MOF) and death. The other progressive changes occurring following hemorrhage outlined on FIG. 1, Cytokine Release; Depressed Lymphocyte and macrophage (MPh) Functions, Immunosuppression, and Increased Susceptibility to Infection, are discussed further below under the Results section of Example 1.

The mode of action of orally administered IL-6 is to locally vasodilate intestinal tissues, leading to increased oxygenation and increased cellular survival. This improved tissue viability is more able to maintain gut barrier function, thereby reducing the likelihood that bacteria and endotoxin will escape into the blood stream. The vasoactivity of IL-6 is a previously unknown quality of this cytokine. The local administration (oral) allows only the intestinal vasculature to be effected, since this cytokine does not reduce systemic blood pressure when given in low doses orally. As stated above, other cytokines in the category inflammatory mediators were tested and were not able to prevent bacterial translocation and could not restore the health of intestinal tissue following hemorrhage.

This application may be useful in scenarios other than hemorrhage. Any traumatic situation in which blood flow to the intestine is reduced may benefit from this therapy. Examples include:

1. Reduction in post-operative ischemia following intestinal transplant. When surgery is carried out on vital organs there frequently is a lag period before the tissue becomes fully oxygenated and begins to function normally. This is especially true in transplanted organs. Organs for transplant have been removed from donors, filled with a preservative solution and kept on ice for various time periods. The amount of time an organ can be stored is dependent on the specific organ. Intestines have a very short in vitro life, and must be transplanted soon after harvest. Following transplantation and restoration of blood flow, local ischemia remains a problem, perhaps due to the stresses placed on the organ during harvest and storage. Further, it has been shown that a certain amount of damage occurs to the intestinal epithelium allowing the possibility of bacterial translocation into the immunosuppressed recipient. Administration of IL-6 intraintestinally—after the organ is removed from the donor and just before being inserted in the recipient, increases local blood flow and allow a higher chance of success in these cases.

2. Similarly, intestinal surgery induces a period of reduced blood flow simply because the surgeon must clamp the superior mesenteric artery to avoid excessive blood loss during the surgical procedure. The subsequent period of ischemia may be shortened by inoculation intraintestinally of a bolus of IL-6, thereby increasing local blood flow and leading to faster healing.

3. Intestinal infection remains a major cause of morbidity and mortality throughout the Third World and in travelers to the area. Translocation of bacteria from the intestine to the blood stream are serious complications of *Salmonella typhi* infections[12] and translation of botulism toxin into the periphery[13].

EXAMPLES

Example 1

BALB/CByJ female mice were obtained from The Jackson Laboratory (Bar Harbor, Me.). They were certified pathogen free, and screening by Charles River Testing Services (Portage, Mich.) showed no serological evidence of viral or parasitic infection. Mice were housed in laminar flow cages in animal facilities at the Naval Medical Research Institute, Bethesda, Md. Standard laboratory animal chow and water was provided ad libitum. Experiments consisted of at least three mice each, the mice each weighing 20–25 g and being about 6–10 weeks old.

Fluoresceinated monoclonal antibodies were obtained from Becton Dickinson (Mountain View, Calif.). Selected experiments were performed using anti Fragment cytophillic-gII/III (Fc-gII/III) receptor antibody (PharMingen, San Diego, Calif.) to block Fc-receptor mediated binding of fluoresceinated antibody prior to staining with fluoresceinated reagents. Flow cytometry was performed on a Fluorescence activated cell sorter (FACS)-STAR Plus cell sorter (Becton Dickinson).

Crude cytokine (CAS) was prepared by a modification of published procedures. In brief, rat spleen cells were adjusted at the time of culture to $5\times10^6$/ml in Dulbecco's Modified Eagle's Medium (DMEM) obtained from GIBCO, Grand Island, N.Y., supplemented with 10% heat-inactivated fetal bovine serum (Intergen, Purchase, N.Y.), 20 mM Hepes, 1 mM sodium pyruvate, 2 mM L-glutamine and $5\times10^{-5}$M 2-mercaptoethanol (2-ME). No antibiotics were added. Con A (Sigma Chemicals, St. Louis, Mo.) was added to a final concentration of 5 mg/ml. The cells were incubated for 48 hours at 37° C., 5% $CO_2$ and the supernatant (CAS) collected. No attempt was made to eliminate the Con A from the resulting cytokine mix. Analysis of the CAS revealed approximately 250 U/ml IL-2, 12 U/ml IL-6, $6\times10^3$ U/ml TNF, that IL-5 and IFN-g were present, and that IL-1 was not present.

Mice were anesthetized by methoxyflurane inhalation (Metofane, Pitman-Moore, Mundelein, Ill.) and maintained under anesthesia by breathing Halothane/$O_2$ (Halocarbon Laboratories, River Edge, N.J.) through a vaporizer (Fluotech-3, Tonawanda, N.Y.). They were cannulated in both femoral arteries using Biotime (Berkeley, Calif.) microcannulas (0.4 mm O.D.) attached to PE-10 tubing. One cannula was connected to a Micro-Med blood pressure analyzer (Louisville, Ky.), and mice were bled over 10 minutes from the opposite femoral artery to a mean arterial pressure (MAP) of 35 mm Hg. During the procedure, the mice were kept warm on an electrical heating pad (Hamilton Aquamatic, Cincinnati, Ohio). Mice were held at 35 mm Hg MAP for one hour, generally by continuing to remove blood being replaced by the natural recovery process, and then resuscitated with shed blood (about 0.7 ml) and 2-fold volume (about 1.4 ml) of Lactated Ringer's Solution (McGowan/Kendall Canada, Ltd., Peterboro, Ontario). The mice were then taken off the anesthesia. After regaining consciousness (approximately 20 minutes to 1 hour after being taken off the anesthesia), they were fed using a curved, 22 gauge ball-tip feeding needle with 0.5 ml culture medium without cytokine; crude cytokine; or culture medium containing 300 units (30 ng) rIL-6(Genzyme, Boston, Mass.). For mice weighing 20–25 g, the rIL-6 dosage was about 1–1.5 μg/kg. As described above, these substances were orally administered (fed) to the mice about 1½ to 2 hours after they were bled. Sham mice were anesthetized and opened for one hour, but not cannulated.

Livers, spleens and mesenteric lymph nodes ("MLN") were removed from mice under aseptic conditions 16 hours post-bleeding. They were weighed and homogenized in 4 ml (Hank's Balanced Salt Solution (HBSS) using an OMNI-2000 homogenizer (OMNI International, Waterbury, Conn.). Serial dilutions were made in Phosphate Buffered Saline (PBS) and plated in 0.1 ml aliquots on sheep blood agar plates (REMEL, Lenexa, Kans.). The plates were inverted and incubated at 37° C. for 24–48 hours and colony counts performed. Data are expressed as bacterial colonies/gm (wet weight) tissue. At the time of sacrifice, the mice were bled under anesthesia and the sera collected and frozen at −70° C. for clinical chemistries.

Mice which had been bled and fed either control fluids or cytokine were sacrificed by cervical dislocation under Metofane anesthesia. Intestines were removed immediately, flushed with fixative consisting of 2% glutaraldhyde and 1% paraformaldehyde, and cut into small (0.5 cm) rings. Intestines were embedded in plastic, cut at 1 m and stained with toluidine blue.

Spleen cells from mice were cultured for 3 days in flat-bottom microtiter plates (Costar, Cambridge, Mass.) at $1\times10^5$ cells/well in MEM (GIBCO) supplemented as described above in the discussion of CAS preparation, except that 100 U/ml penicillin, 100 μg/ml streptomycin and 50 μg/ml gentamicin sulfate were added. Con A was added at the amounts indicated. At the end of the incubation period, 0.8 microcuries (μCi) $^3$H-thymidine (DuPont NEN Research Products, Boston, Mass.) was added for a further 6 hours. The cells were harvested with a Tomtec 96 harvester on fiber glass filters and counted in a Betaplate liquid scintillation counter (Wallac, Gaithersburg, Md.). Results are expressed as mean cpm/well ±SD.

For Mixed Lymphocyte Reaction (MLR) spleen cells were prepared as above but, instead of being cultured with Con A, they were cultured with $5\times10^5$ irradiated C57B1/6 cells as allogeneic stimulators or irradiated BALB/c spleen cells as syngeneic stimulated controls. Plates were incubated for five days, then pulsed and harvested as above.

Figure 2:
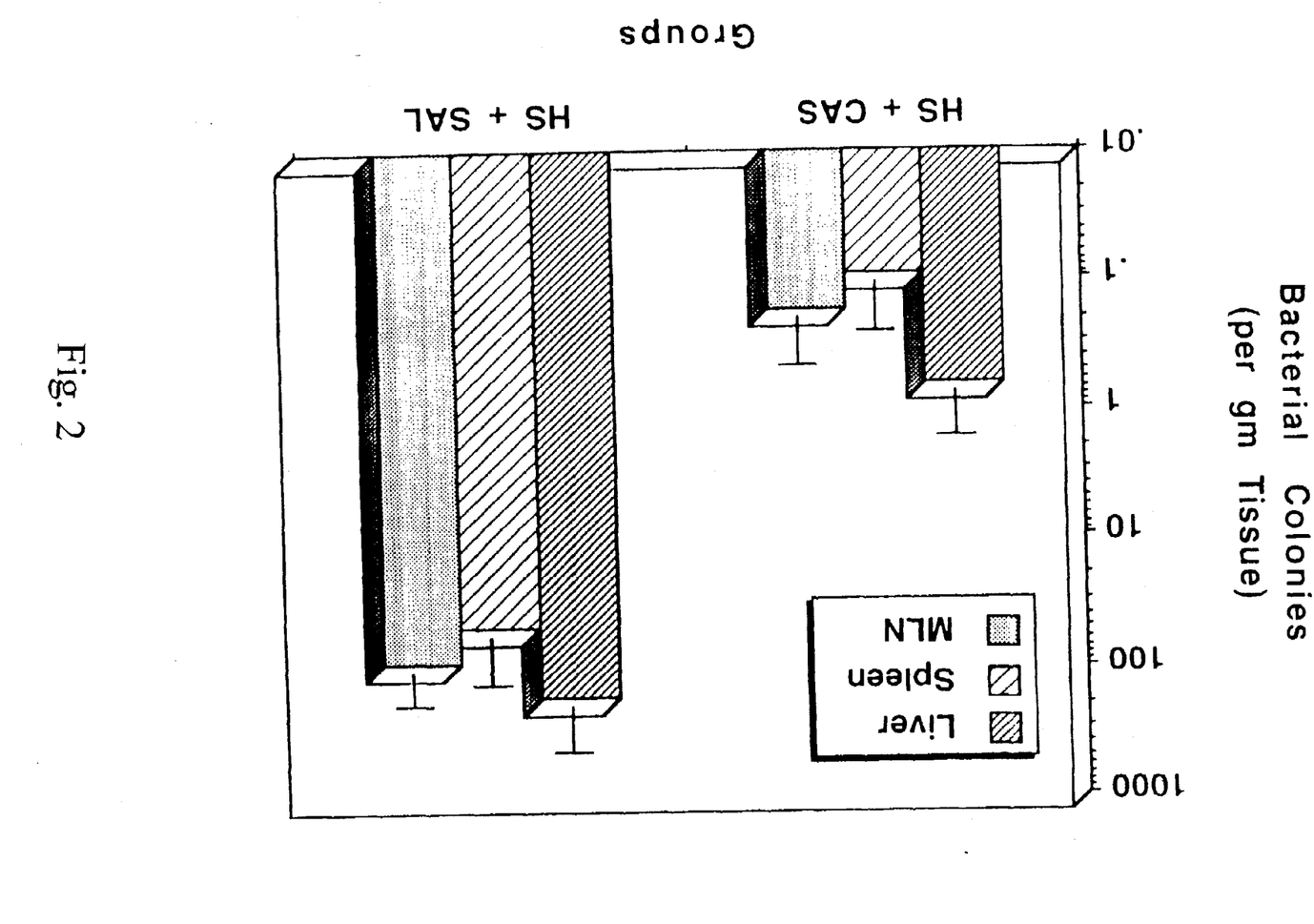
FIG. 2 shows the growth of bacteria in the liver, spleen, and mesenteric lymph nodes of haemorrhaged mice fed either media and saline and mice fed media and Concanavalin A supernatant ("CAS") as measured 16 hours post-haemorrhage.

Results:

As to the question of translocation of bacteria from the gut to other organs, bacteria were recovered at 16 hours post-bleeding from livers, spleens and mesenteric lymph nodes of mice. The results are shown in FIG. 2 as a combination of data from 8 experiments performed as described above. Mice fed saline (SAL) approximately 1 hours post hemorrhage had over 200 colonies/gram of liver, while those fed crude cytokine (CAS) showed significantly reduced bacterial colonies, on the order of 0.8 colonies/gram of liver (P<0.001). Comparable results obtained for the spleens and mesenteric lymph nodes. Other experiments performed as above except that the mice were given oral cytokine 4 hours after being taken off the anesthesia, have shown that crude cytokine given as late as 5 hours post hemorrhage could reduce the numbers of bacteria translocating to the livers of mice by approximately the same amount.

Previous work in the Campylobacter model[14] showed that orally administered IL-6 significantly reduced the numbers of pathogenic bacteria in the intestines of treated mice. The present invention differs from that work in that the present invention is a method for ameliorating the effects of hemorrhagic shock in a subject by locally administering to the gut of the subject, at a selected time during the period of from about 5 hours before blood loss to about 5 hours after blood loss, a therapeutic amount of a cytokine. The amelioration of the adverse effects of hemorrhagic shock was an unexpected result and is not obvious in light of the referenced previous work.

Figure 3:
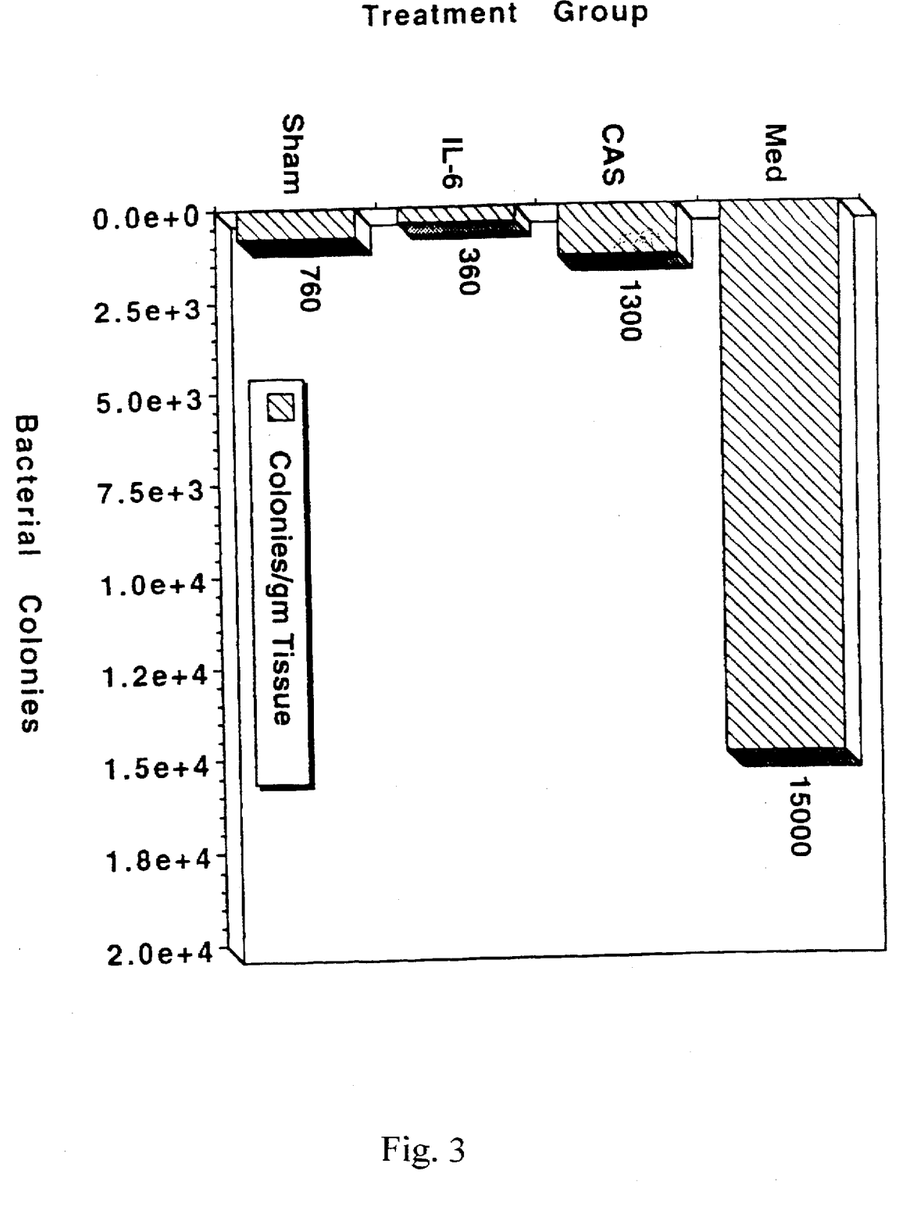
FIG. 3 shows the growth of bacteria in the liver of haemorrhaged mice fed either control media, CAS and rIL-6 as measured 16 hours post-haemorrhage and in the liver of a non-haemorrhaged (sham) mouse.

In this experiment (Experiment 1), the sham group was not bled. The other mice were bled and fed cytokine free medium, CAS, or rIL-6, specifically, 300 U recombinant human IL-6 (yeast-derived rhIL-6) supplied by Genzyme. The dosage was about 30 ng for each mouse and since each mouse weighed about 20–25 g, the dosage was about 1200–1500 ng (1.2–1.5 µg) rIL-6/kg of subject body weight. As with the CAS treatment, the bacterial colonies were measured in liver 16 hours after bleeding. For the sham group, the bacterial colonies were measured in liver. The results, as shown in FIG. 3 for individual mice, demonstrate that rIL-6 was equal to, or better than, CAS at restricting the translocation of bacteria from the gut to the liver. These experiments were repeated six times over a period of six months and gave similar results.

Figure 4:
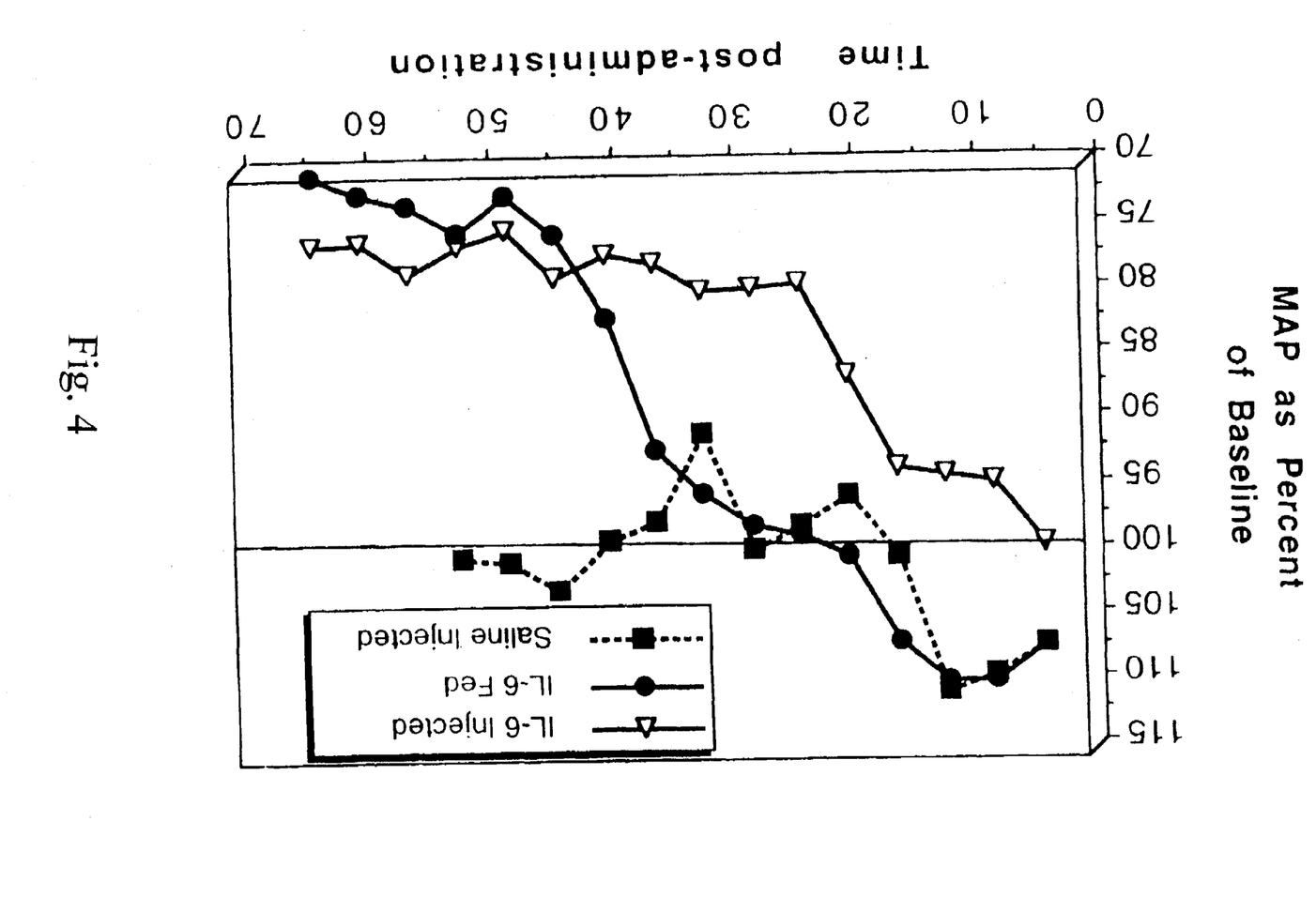
FIG. 4 shows the measurement over time of blood pressure, calculated as percent of pre-administration Mean Arterial Pressure (MAP) normalized to each animal.

Mice were anesthetized and cannulated as above. Their blood pressure was monitored until it stabilized for 30 minutes and, at that time, instead of being hemorrhaged, mice were given 300 units rhIL-6 orally or intravenously. In a representative experiment shown in FIG. 4, the mice receiving rIL-6 showed a rapid reduction in blood pressure compared to the media-fed control mouse over a 64 minute time period. This experiment demonstrates that rIL-6 lowers the central blood pressure by vasodilation: it counteracts the shunting of blood from the intestine and reopens intestinal blood flow. As therapy for a patient subjected to hemorrhagic shock, measures would need to be taken to restore overall blood pressure, for example by administering plasma and fluids. Oral administration of rIL-6 helps to restore intestinal integrity.

Since immunosuppressive phenomena have been described following severe hemorrhagic shock[15], an investigation into immune capacity was undertaken. Spleen cells from normal and sham mice responded vigorously to Con A. Spleen cells from hemorrhaged mice fed culture media proliferated significantly less, while those fed CAS were capable of somewhat increased proliferation, and those fed rIL-6 returned approximately to normal. This experiment was repeated at least five times with different shipments of mice and different lots of rIL-6. Mesenteric lymph node cells showed a similar pattern of proliferation to that seen in spleens (data not shown).

Since it is often difficult to show active suppression in a mitogen-stimulated culture because of the large number of clones involved[16], an MLR with a limited number of potential responders was used for the examination of suppression. The capacity of BALB/c spleen cells to proliferate in response to H-2 antigen on the surface of irradiated allogeneic (C57B1/6) spleen cells was examined. Proliferative controls included BALB/c spleen cells incubated with irradiated syngeneic (BALB/c) cells. For simplicity, these results are not shown but fall within acceptable limits as described for an MLR. To test for the presence of suppressor cells, varying numbers of spleen cells from hemorrhaged mice were cultured together with a fixed number ($5\times10^5$) of spleen cells from normal mice in the presence of irradiated allogeneic stimulator cells. The counts observed with cell mixtures were not less than the expected (additive) values. There may be some synergistic effect. These data do not indicate the presence of active suppression of proliferation in this MLR. Cells from normal mice were able to proliferate in response to a fixed number ($5\times10^5$) of irradiated allogeneic spleen cells in linear fashion (r2=0.99), suggesting that crowding is not a factor in the mixtures. Spleen cells from mice bled and given either media or CAS were unable to proliferate in response to alloantigen. These data suggest that either cells capable of response to the mitogen are present in reduced numbers or that T-cells are present in normal numbers but have reduced capacity to proliferate.

In order to determine if the reduction in cell proliferation was the result of reduced T-cells in the spleens of hemorrhaged mice, flow cytometry experiments were conducted. The number of CD 3+ cells in spleens of hemorrhaged mice fed CAS or media was similar but reduced below the number of CD 3+ cells taken from control mice at 16 hours post-hemorrhage. The percent of cells staining positively for CD 4 and CD 8 was also proportionately reduced, as was the percent of cells positive for CD 45R (B220). These results compare well with those described by Cheadle et al.[17] and suggest that loss of cell number may be an explanation of why reduced proliferative capacity is found in peripheral lymphoid cells of hemorrhaged mice. This finding does not, however, explain the restoration of T cell function by oral cytokine administration seen in hemorrhaged mice fed cytokine. It may be concluded, therefore, that reduced capacity to proliferate is a valid explanation for the reduced proliferative responses observed in the spleens of hemorrhaged mice.

Figure 5:
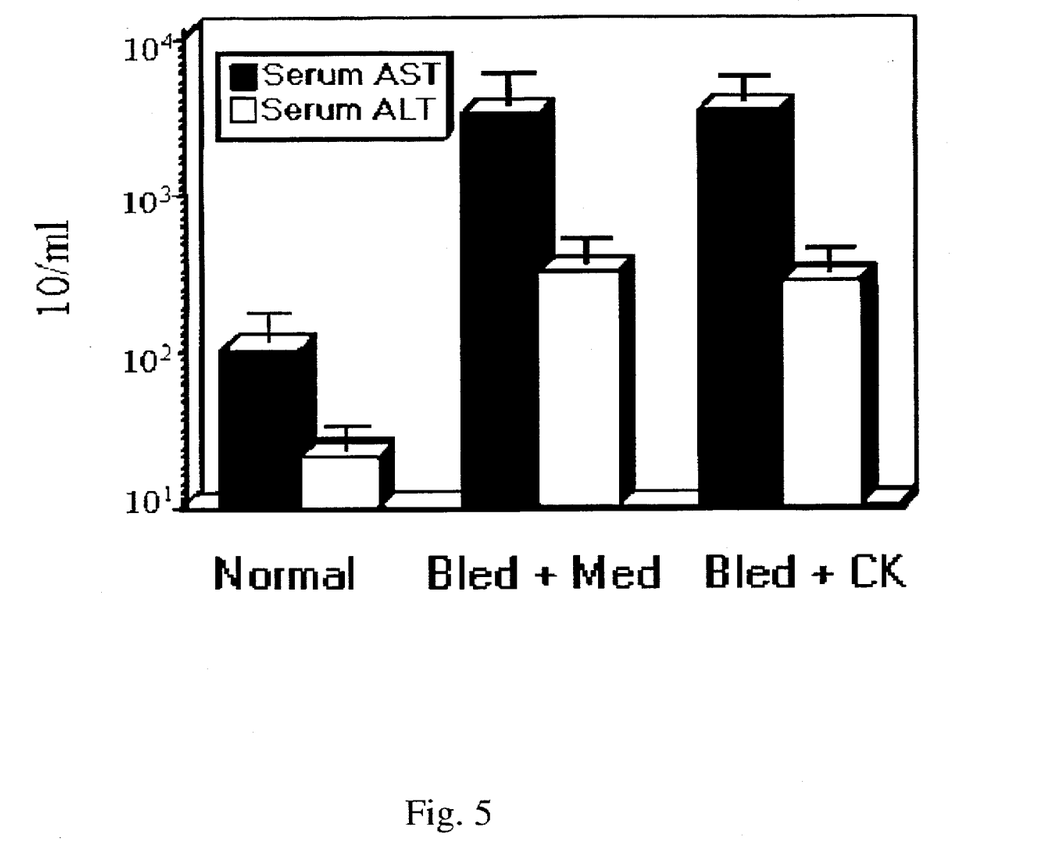
FIG. 5 shows the levels of liver function enzymes, in particular serum Aspartate amino transferase AST (Serum glutamyl oxalo transaminase (SGOT)) and Alanine amino transferase (ALT)) (serum glutamyl puryvic transferase (SGPT)), for mice fed either media or CAS after hemorrhage, and for mice that were not bled.

Although oral administration of cytokine, and especially CAS, and most especially IL-6, was useful in eliminating bacterial translocation following hemorrhage, it was unknown whether other consequences of shock could be affected by this regimen. In order to determine systemic effects of hemorrhage, liver function enzymes, in particular serum AST (SGOT) and ALT (SGPT) were analyzed in mice fed either media or CAS after hemorrhage, and compared with the values for mice that were not bled. The results of these tests are compared for five mice in each group. Referring now to FIG. 5, both AST and ALT values are significantly higher in hemorrhaged mice than in normal mice. CAS feeding was ineffective in reversing the elevations of serum AST/ALT seen in mice under both bled conditions. Since the serum liver enzymes were the same in mice hemorrhaged and fed CAS when compared with mice fed just media, it can be concluded that the cytokine effects may be purely a local phenomenon, with little systemic consequences. These data suggest that multiple insults are seen following hemorrhage in mice, only some of which are reversible by administration of cytokines.

Jejunal segments taken from normal mice, hemorrhaged mice fed media and hemorrhaged mice fed rIL-6 were compared. The sections from normal mice showed intact jejunal mucous membranes in all sections. The villus morphology was consistent throughout all normal samples with villi forming uniformly long finger-like processes arranged in leaf-like patterns with 2–5 villi apposed side-by-side. The edges of the villi were generally smooth and straight. The tips of villi were relatively rounded, without sharp or pointed contours. The villus processes were 3–4 times longer than jejunal crypts.

Sections of jejunum from mice that had been hemorrhaged and fed saline showed a remarkable change in villus morphology. Now, the villi were separated by wide spaces and broad leaf-like patterns of fronds were no longer apparent. The edges of the villi were not straight and smooth, but instead were relatively deeply scalloped through their lengths. In several foci, short folds appeared to extend from the surface of the villi. The tips of the villi were more irregular and not rounded, some having tongue-like shapes. The lengths of the villi and crypts remained normal.

Sections of jejunum from mice that had been hemorrhaged and treated with cytokines showed jejunal villus morphology restored to a normal appearing, finger-like pattern with straight and smooth edges to the fronds. Scattered fronds appeared somewhat shorter in length than those observed in the normal jejunal sections, but were not representative of an overall pattern of blunting. No significant scalloping of the villus edges was seen in these sections. It is apparent that the intestines from mice hemorrhaged and treated with cytokines were healthier than those hemorrhaged and not treated with cytokines.

In all sections, scattered mucous secreting cells were arranged along the columnar epithelium of the villi. Epithelial cells had mid-to-basal located oval nuclei along the villus fronds. Epithelial brush borders appeared to be intact throughout the villus processes. Crypts showed cells containing basal nuclei and abundant secretory granules. Scattered mitoses were present in the basal regions of the membrane. Each villus showed normal appearing cores of lamina propria composed of loose connective tissue having delicate vessels and capillaries through-out. The muscularis mucosa and submucosa appeared unremarkable throughout. No inflammatory infiltrates were present in the jejunal wall. The histological changes seemed limited to ileum and jejunum. No changes were seen in proximal duodenum or colon. These observations suggest that only areas supplied by the superior mesenteric artery are affected by ischemic damage.

Example 2

Other than as described below, this experiment was carried out the same as Example 1, except on rats rather than on mice.

Male Sprague-Dawley rats were obtained from Taconic Farms, (Germantown, N.Y.) and weighed 250–300 gm each.

Anesthetized rats were bled from the carotid artery at a rate of 15 ml/kg at 1 ml/minute. Bacteriological cultures of livers and mesenteric lymph nodes from hemorrhaged animals given recombinant IL-6 had significantly fewer colonies per gram of tissue than saline-fed controls. $^{125}$I-labeled IL-6 remained in the gut for up to 6 hours giving regional protection, while labeled IL-2 was disseminated throughout the body in the same time. In vivo and in vitro studies of IL-6 showed that long incubations with high doses of trypsin, chymo-trypsin or with intestinal contents were necessary to inactivate the bioactivity of this cytokine. The rats were anesthetized with a combination of thiobutabarbital (90 mg/kg, IP) and ketamine (75 mg/kg, IM). Using aseptic technique, PE-50 polyethylene catheters were inserted into the jugular vein and carotid artery for blood withdrawal and cardiovascular monitoring, respectively. The animals were subjected to a 15 ml/kg hemorrhage, representing one fourth of their estimated total blood volume, at a rate of 1 ml/minute; the rats were not resuscitated. At the end of blood withdrawal, the mean blood pressure was 30–45 mm Hg. Immediately following the hemorrhage, an 8 cm full-thickness skin incision on the dorsum of the rats was made. The wound was closed with silk sutures one hour after the incision. The rats were not resuscitated. One hour following hemorrhage, the rats were fed 300 units (30 ng) of IL-6 in 0.5 ml saline or 0.5 ml saline alone (control). Since the rats weighed 250–300 g, the IL-6 dosage was 100–120 ng/kg.

Rat livers were removed under aseptic conditions 48 hours post hemorrhage. These were the times of maximum bacterial translocation, as determined previously. The livers were weighed and homogenized in HBSS using an OMNI-2000 homogenizer (OMNI International, Waterbury, Conn.). Serial dilutions were made in PBS and plated in 0.1 ml aliquots on sheep blood agar plates (REMEL, Lenexa, Kans.). The plates were inverted and incubated at 37° C. for 24–48 hours and colonies were counted. Data are expressed as bacterial colonies/gm (wet weight) tissue.

Data from individual animals in each group were submitted to analysis of variance (ANOVA). The data for each group were then compared using SAS[18]. Significance was determined by two-tailed Student's t test using the computer program Statview II (Abacus Concepts, Inc., Berkeley, Calif.) and is reported as P value where observed between control and treated groups.

TABLE I

| Treatment[a] | Colonies/gm Tissue[b] Liver |
| --- | --- |
| Saline | 3,393 ± 238 |
| Oral IL-6 | 126 ± 34 |

The foregoing descriptions of the preferred embodiments are intended to be illustrative and not limiting. It will be appreciated that numerous modifications and variations can be made without departing from the spirit or scope of the present invention.

References

1. Baker, J. W., E. A. Deitch, M. Li, R. D. Berg and R. D. Specian (1988) Hemorrhagic shock induces bacterial translocation from the gut. J. Trauma 28:896–904.

Deitch, E. A. (1990) Bacterial translocation of the gut flora. J. Trauma 30:S184–S189.

Bark, T. et al. (1993). Bacterial translocation after non-lethal hemorrhage in the rat. Circ. Shock. 41:60–65.

2. See note 1, supra.

3. Ertel, W., M. H. Morrison, A. Ayala, R. E. Dean, and I. H. Chaudry (1992) Interferon-gamma attenuates hemorrhage-induced suppression of macrophage and splenocyte functions and decreases susceptibility to sepsis. Surgery 111:177–187.

Abraham, E., and A. A. Freitas (1989) Hemorrhage produces abnormalities in lymphocyte function and lymphokine generation. J. Immunol. 142:899–906.

Stephan, R. N., A. Ayala, J. M. Harkema, R. E. Dean, J. R. Border, and I. H. Chaudry (1989) Mechanism of immunosuppression following hemorrhage: defective antigen presentation by macrophages. J. Surg. Res. 46:553–556.

Zapata-Sirvent, R. L., J. F. Hansbrough, M. C. Cox, and W. H. Carter (1992) Immunologic alterations in a murine model of hemorrhagic shock. Crit. Care Med. 20:508–517.

4. Rush, B. F. 1989. Irreversibility in hemorrhagic shock is caused by sepsis. The American Surgeon 55:204.

5. VanSnick, J. Interleukin-6: an overview. Ann. Rev. Immunol. 8:253. 1990.

6. Helle, M., L. Boeije, and L. S. Aarden. Functional discrimination between interleukin 6 and interleukin 1. Eur. J. Immunol. 18:1535. 1988.

7. Ryffel, B and M. Weber. Preclinical safety studies with recombinant human Interleukin-6 (rhIL-6) in the primate *Callithrix jacchus* (marmoset): comparison with studies in rats. J. Appl. Toxicol. 15:19–26. 1995.

Andrews, A. E., G. J. Barcham, K. Ashman, E. J. T. Meeusen, M. R. Brandon and A. D. Nash. Molecular cloning and characterization of a ruminant interleukin-6 DNA. Immunol. and Cell Biol. 71:341–348.

8. Ryffel, B., M. J. Mihatsch and G. Woerly. Pathology induced by IL-6. Int. Rev. Exp. Pathol. 34:79–89.

Heinrich, P. C., J. V. Castell and T. Andus. Interleukin-6 and the acute phase response. Biochem. J. 265:621–636. 1990.

9. Baqar, S., N. D., Pacheco, and F. M. Rollwagen. Dec. 1993. Modulation of Mucosal Immunity against *Campylobacter jejuni* by Orally administered Cytokines. Antimicrobial Agents and Chemotherapy, Vol.37, no. 12, p.2688.

10. See, VanSnick. J., supra note 5.

11. Buttgereit F., and M. D. Brand. A hierarchy of ATO-consuming processes in mammalian cells. Biochem J. 312:163–167. 1995.

12. Rasaily, R., P. Dutta, M. R. Saha, U. Mitra, M. Lahiri and S. C. Pal. Multi-drug resistant typhoid fever in hospitalised children. Clinical, bacteriological and epidemiological profiles Eur. J. Epidemiol. 1994 10: 41–6.

Saha, M. R., P. Dutta, S. K. Bhattacharya, R. Rasaily, U. Mitra, D. Dutta, M. D. Bhattacharya and S. C. Pal. Occurrence of multi-drug resistant *Salmonella typhi* in Calcutta. Indian J. Med. Res. 1992 95: 179–80

13. Woodruff, B. A., P. M. Griffin, L. M. McCroskey, J. F. Smart, R. B. Wainwright, R. G. Bryant, L. C. Hutwagner, and C. L. Hatheway. Clinical and laboratory comparison of botulism from toxin types A, B, and E in the United States, 1975-1988. J. Infect. Dis. 1992 166: 1281–6.

14. Baqar S., N. D. Pacheco, and F. M. Rollwagen (1993) Modulation of mucosal immunity against *Campylobacter jejuni* by orally administered cytokines. Antimicrob. Agents Chemother. 37:2688–2692.

15. Ertel, W., Morrison M. H., Ayala A., Dean R. E. and Chaudry, I. H., supra note 3.

16. Rollwagen F. M., and Stutman. O. (1981) Culture generated suppressors: evidence for an adherent cell component. Cell. Immunol. 64:371–380.

17. Cheadle W. G., Pemberton, R. M., Robinson, D., Livingston, D. H., Rodriguez, J. L., and Polk, H. C., Jr. (1993) Lymphocyte subset responses to trauma and sepsis. J. Trauma. 35:844–849.

18. SAS User's Guide: Statistics version 5. SAS Institute, Gary N.C., 1985.

What is claimed is:

1. A method for ameliorating the effects of hemorrhagic shock in a subject by mitigating extraintestinal translocation of enteric bacteria, said method comprising the step of locally administering to the gut of the subject at a selected time during the period of from about 5 hours before blood loss to about 5 hours after blood loss, a pharmaceutical/therapeutic composition containing between about 40 nanograms and about 1 milligram of interleukin-6 for each kilogram of the subject's weight.

2. A method for ameliorating the effects of hemorrhagic shock in a subject by mitigating extraintestinal translocation of enteric bacteria, said method comprising the step of orally administering to the subject at a selected time during the period of from about 5 hours before blood loss to about 5 hours after blood loss, a pharmaceutical/therapeutic composition of between about 40 nanograms and about 1 milligram of interleukin-6 for each kilogram of the subject's weight.

3. The method of claim 2 further comprising orally administering the interleukin-6 to the subject by use of a naso-gastric tube.

4. The method of claim 1 wherein the pharmaceutical/therapeutic composition contains yeast-produced recombinant interleukin-6.

5. The method of claim 1 wherein the pharmaceutical/therapeutic composition contains at least about 80 nanograms of interleukin-6 for each kilogram of the subject's weight.

6. The method of claim 5 wherein the pharmaceutical/therapeutic composition contains at least about 150 nanograms of interleukin-6 for each kilogram of the subject's weight.

7. The method of claim 5 wherein the pharmaceutical/therapeutic composition contains at most about 3 micrograms of interleukin-6 for each kilogram of the subject's weight.

8. The method of claim 7 wherein the pharmaceutical/therapeutic composition contains at most about 1.5 micrograms of interleukin-6 for each kilogram of the subject's weight.

9. The method of claim 2 wherein the subject is a mammal.

10. The method of claim 9 wherein the subject is a human being.

11. The method of claim 2 wherein the selected time for administration is during the period from the time of blood loss to about 5 hours later.

12. The method of claim 2 wherein the pharmaceutical/therapeutic composition contains yeast-produced recombinant interleukin-6.

13. The method of claim 1 wherein the subject is a mammal.

14. The method of claim 13 wherein the subject is a human being.

15. The method of claim 1 wherein the selected time for administration is during the period from the time of blood loss to about 5 hours later.

16. The method of claim 6 wherein the pharmaceutical/therapeutic composition contains at most about 1.5 micrograms of interleukin-6 for each kilogram of the subject's weight.

17. The method of claim 2 wherein the pharmaceutical/therapeutic composition contains at least about 80 nanograms of interleukin-6 for each kilogram of the subject's weight.

18. The method of claim 17 wherein the pharmaceutical/therapeutic composition contains at least about 150 nanograms of interleukin-6 for each kilogram of the subject's weight.

19. The method of claim 17 wherein the pharmaceutical/therapeutic composition contains at most about 3 micrograms of interleukin-6 for each kilogram of the subject's weight.

20. The method of claim 19, wherein the pharmaceutical/therapeutic composition contains at most about 1.5 micrograms of interleukin-6 for each kilogram of the subject's weight.

21. The method of claim 18 wherein the pharmaceutical/therapeutic composition contains at most about 1.5 micrograms of interleukin-6 for each kilogram of the subject's weight.

* * * * *